United States Patent

Romine

[11] 3,954,798
[45] May 4, 1976

[54] PROCESS FOR PREPARING PHOSPHOROTRIAMIDOTHIOATES

[75] Inventor: Hugh E. Romine, Ponca City, Okla.

[73] Assignee: Continental Oil Company, Ponca City, Okla.

[22] Filed: Aug. 19, 1974

[21] Appl. No.: 498,345

[52] U.S. Cl. .................. 260/326.5 A; 252/46.7
[51] Int. Cl.² ........................ C07D 207/12
[58] Field of Search ................ 260/326.5 A

[56] References Cited
UNITED STATES PATENTS

| | | | |
|---|---|---|---|
| 2,411,527 | 11/1946 | Dickey et al. | 260/461 |
| 2,552,574 | 5/1951 | Moyle et al. | 260/461 |
| 2,615,037 | 10/1952 | Moyle | 260/461 |
| 2,865,948 | 12/1958 | Fusco | 260/461 |
| 3,244,586 | 4/1966 | Rigertink | 424/202 |
| 3,278,550 | 10/1966 | Norman et al. | 260/326.2 |
| 3,286,002 | 11/1966 | Curtis et al. | 260/947 |
| 3,634,241 | 1/1972 | Lowe et al. | 260/326.2 X |
| 3,733,379 | 5/1973 | Szabo | 260/950 |

*Primary Examiner*—Dale R. Ore
*Attorney, Agent, or Firm*—Bayless E. Rutherford, Jr.

[57] ABSTRACT

A process is disclosed for preparing novel compounds represented by the formula

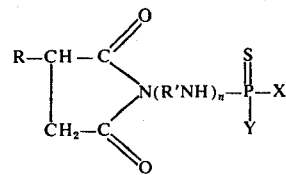

wherein R is a $C_{10}$–$C_{100}$ alkylene group, R' is a $C_1$–$C_5$ alkylene group, $n$ is an integer of 1 to 4, X is $NH_2$, NHR'', or NR''R'', and Y is $NH_2$, NHR'', NR''R'', or halogen, wherein, R'' is an alkyl or alkylene polyamino group. The process comprises:

1. reacting thiophosphoryl chloride with a monoamine (e.g., diethylamine) to give a reaction product comprising about 60 to about 100 mole percent phosphorochloridodiamidothioate and about 0 to about 40 mole percent phosphoroamidodichloridothioate;
2. reacting the reaction product of step (1) with an alkylene polyamine to give a phosphorotriamidothioate;
3. reacting the phosphorotriamidothioate of step (2) with an alkenyl succinic anhydride or acid; and
4. treating the reaction product of step (3) with a basic material to give the desired product. The product of the process is useful as an additive in lubricating oils.

9 Claims, No Drawings

PROCESS FOR PREPARING PHOSPHOROTRIAMIDOTHIOATES

CROSS-REFERENCE TO RELATED APPLICATIONS

Application Ser. No. 484,024, filed June 28, 1974, and having the same inventor and assignee, is directed to the following:

a. the novel compounds per se;
b. lubricating oils containing the novel compounds; and
c. a process for preparing the novel compounds.

FIELD OF THE INVENTION AND BACKGROUND

Field of the Invention

The invention is in the general field of materials which are suitable for use as additives in lubricating oils. In particular, the invention is in the field of preparing materials which provide lubricity, oxidation inhibition, and dispersancy in lubricating oils.

Background

Various materials have been used in lubricating oils for many years. These materials, known as "lube additives," serve a variety of functions. For example, compounds containing phosphorus, sulfur, or chlorine and combinations thereof have been used as lubricity agents. This type of material serves to improve the load-carrying property of the lubricant. Other materials (e.g., zinc dithiophosphates, phenols, or aryl amines) are known which improve the oxidation stability of lubricants. Still further, other materials have been used to impart a dispersancy property to lubricants. These materials serve to disperse wear products and other foreign materials in the lubricant.

For many years various types of oil-soluble sulfonates have been used as dispersants in lubricants. The preferred oil-soluble sulfonates have been the barium and calcium sulfonates. More recently, an interest has developed in the use of dispersants which do not contain any metal. This latter type of dispersant is referred to as an "ashless dispersant." A particularly preferred type of ashless dispersant contains the polyalkyleneamine moiety. Unfortunately, this type of material is inherently unstable to oxidation.

I have discovered a novel process for preparing certain novel compounds which are useful in lubricating oils.

Prior Art

An IFI-Plenum computer search failed to produce a reference disclosing the novel compounds of my invention. Also, a search by Washington searcher failed to produce a reference disclosing the novel compounds of my invention or the process of preparing them. For the record, the Washington searcher did call attention to the following patents which are of general interest: U.S. Pat. Nos. 2,552,574; 3,244,586; 3,286,002; 2,411,527; 2,615,037; 2,865,948; and 3,733,379.

Brief Summary of the Invention

Broadly stated, the present invention is directed to a process for preparing compounds represented by the formula

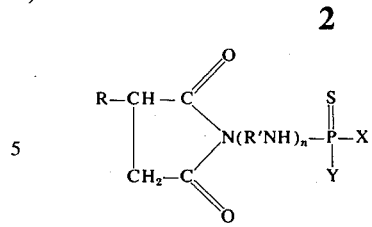

wherein R is an alkenyl group containing 10 to 100 carbon atoms; R' is an alkylene group containing 1 to 5 carbon atoms; n is an integer of 1 to 4; X is selected from the group consisting of $NH_2$, $NR''R''$, and $NHR''$; and Y is selected from the group consisting of $NH_2$, $NR''R''$, $NHR''$, and halogen, preferably chlorine or bromine, wherein, in X and Y, R'' is a $C_1$–$C_{16}$, preferably $C_1$–$C_5$, alkyl group, or alkylene polyamino group containing 1 to 20 carbon atoms.

The process of my invention comprises:

a. reacting thiophosphoryl chloride with a monoamine (e.g., diethylamine) to give a reaction product comprising about 60 to about 100 mole percent phosphorochloridodiamidothioate and about 0 to about 40 mole percent phosphoroamidodichloridothioate;
b. reacting the reaction product of step (a) with an alkylene polyamine to give a phosphorotriamidothioate;
c. reacting the phosphorotriamidothioate of step (b) with an alkenyl succinic anhydride or acid; and
d. treating the reaction product of step (c) with a basic material to give the desired product.

DETAILED DESCRIPTION

Materials Used

In addition to thiophosphoryl chloride ($PSCl_3$), any combination of $P_4S_{10}$ and HCl which yields $PSCl_3$ in situ can be used.

Suitable monoamines to prepare a reaction product comprising about 60 to about 100 mole percent phosphorochloridodiamidothioate and about 0 to about 40 mole percent phosphoroamidodichloridothioate are those which yield the radicals $NH_2$, $NR''R''$, and $NHR''$ wherein R'' is as described previously. Primary $C_2$–$C_6$ aliphatic amines are preferred. Examples of suitable monoamines include ammonia, dimethylamine, diethylamine, dibutylamine, dihexylamine, didecylamine, dihexadecylamine, methylethylamine, methylbutylamine, ethyldecylamine, N,N-ethyl ethylbenzene amine, N,N-butyl propylbenzene amine, N,N-butyl diethylbenzene amine, monoethylamine, monobutylamine, monodecylamine, and monohexadecylamine.

Acceptor — in describing the preparation of the phosphoroamidothioates, the term "acceptor" is used. This term refers to materials which react with (or "accept") HCl. Examples of suitable acceptors include the monoamines described in the foregoing and inorganic oxides such as CaO, MgO, and the like.

Suitable alkylene polyamines for use in my process are represented by the formula

wherein R' is an alkylene group containing 1 to 5, preferably 1 to 2, carbon atoms and n is an integer of 1 to 4. Ethylene diamine is a preferred alkylene polyamine. Other suitable alkylene polyamines include diethylene triamine, triethylene tetraamine, tetraethylene pentamine, and tetrapentylene pentamine.

Suitable alkenyl succinic anhydrides are those in which the alkenyl group contains 10 to 100 carbon atoms. Preferably, the alkenyl group contains 12 to 50 carbon atoms. Examples of suitable alkenyl groups include polyisobutenyl, polybutenyl, polyisopropenyl, polypropenyl, polyisopentenyl, and polypentenyl. In addition to alkenyl succinic anhydrides, the analogous alkenyl succinic acids can be used.

Preparation of the Phosphorochlorodiamidothioates and phosphoroamidodichloridothioates The reaction for this step of the process can be shown as follows:

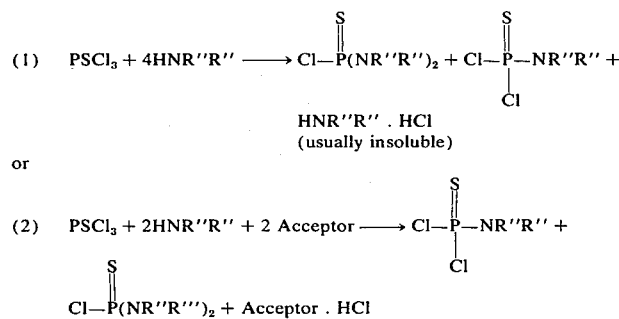

From the above-described reactions, it is apparent that when the acceptor is an amine, the reaction requires twice as much amine as when a non-amine is the acceptor.

Also, in the above-described reaction $R''$ is restricted to $C_1$–$C_{16}$ alkyl groups.

More specifically, the amount of $PSCl_3$ to amine in the reaction can be stated as follows on a molar basis.

| | |
|---|---|
| Suitable range | 1.0 to 5.0 |
| Preferable range | 1.5 to 4.0 |

While theoreticaly the reaction does not require the presence of a solvent, since the reaction is exothermic usually a solvent is desirable in order to control reaction temperature. Generally, any solvent is suitable in which the reactants (e.g., $PSCl_3$, etc) are soluble. Preferably, the solvent is one in which, in addition, the amine salts are insoluble. Typical examples of suitable solvents include benzene, toluene, p-dioxane, diethyl ether, bis-2-methoxyethyl ether, and dimethylformamide.

The reaction can be conducted at any convenient temperature below the boiling point of the lowest boiling reactant (or solvent). Generally, the temperature can be in the range of about 0° to 110°C. Typically, ambient temperatures are employed.

Control of pressure is not required. Any convenient pressure can be used.

Inasmuch as the reaction is exothermic, the amine is added to the $PSCl_3$ incrementally. Typically, the time of addition is 1 to 4 hours in the laboratory. Conceivably, the time of addition could be much longer—e.g., 24–48 hours; however, such is not practical.

Preparation of Phosphorotriamidothioates By Reaction of the Phosphorochloridodiamidothioate and Phosphoroamidodichloridothioate With an Alkylene Polyamine Using ethylene diamine as the alkylene polyamine, the reaction for this step of the process can be shown as follows:

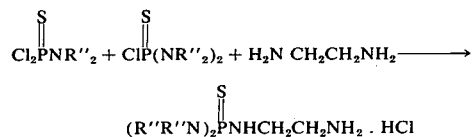

In the reaction shown immediately preceding, the formation of the triamido compound is not necessarily complete. Accordingly, some bound chlorine can be present in the product.

On a molar basis, the amount of polyalkylene amine to amide is as follows:

| | |
|---|---|
| Suitable | 0.5 to 10 |
| Preferred | 1 to 5 |

A hydrogen chloride acceptor may be substituted 1 for 1 on a mole equivalent basis for up to one-half of the alkylene polyamine.

While not absolutely necessary, usually the reaction is conducted in the presence of an inert solvent which functions as a diluent. Typical examples of suitable solvents include benzene, toluene, p-dioxane, and bis-2-methoxyethyl ether.

The reaction can be conducted at any convenient temperature up to 110°C or the boiling point of the solvent or reactants. Usually the temperature is in the range of ambient (20°–30°C) to 50°C.

Control of pressure is not required. Any convenient pressure can be used.

The reaction time is not critical and can be determined by any person skilled in the art. Typically, the reaction time is in the range of about ½ to about 4 hours.

Typically a filtration step is used to remove insoluble chloride salts.

Reaction of the Phosphorotriamidothioates and the Alkenyl Succinic Anhydrides (or Acids)

In conducting this reaction, the amounts of amide to anhydride (or acid), on a molar basis, are as follows:

Suitable range        0.5 to 2.5
Preferred range       0.8 to 2.0

It is desirable to use a diluent-solvent in this step which facilitates removal of water by azeotropic distillaton. Knowing this, any person skilled in the art can determine a suitable solvent. Typical examples of suitable solvents include benzene and toluene.

Typically, the reaction is conducted near the boiling point of the solvent which is usually above 70°C. Any convenient pressure can be used.

The reaction time is not critical and can be determined by any person skilled in the art. Typically, the reaction time is 1 to 24 hours but can be as long as 72 hours.

Treatment of the Reaction Product of the Phosphorotriamidothioate and Alkenyl Succinic Anhydride (or Acid) With a Basic Compound As indicated in the equations illustrating the process, the initial reaction product may contain residual chlorine. The properties of the final product as a lube oil additive are affected by the presence of residual chlorine. Generally, it is preferred to remove all active chlorine. However, the presence of bound chloride may be desirable.

The reaction product is treated with a basic material (or a hydrogen chloride acceptor) to effect reduction of the chloride content. Examples of suitable basic materials (or hydrogen chloride acceptors) include metal oxides (e.g., CaO), amines (ammonia, primary, secondary, or tertiary), and metal alkoxides (e.g., sodium methoxide).

Knowing that the reaction product is to be treated with a basic material, any person skilled in the art can readily determine the exact details. Typically, the treatment is conducted by adding the basic material to the reaction product and maintaining a temperature of about 50° to about 150°C for a time in the range of ½ to 24 hours. The amount of basic material usually is at least one equivalent per mole of phosphorotriamidothioate used to prepare the crude reaction product. The reaction admixture is then cooled to room temperature, filtered to remove suspended salts, and distilled to remove excess basic material (if liquid) and any solvent present.

In order to disclose the nature of the present invention still more clearly, the following examples will be given. It is to be understood that the invention is not to be limited to the specific conditions or details set forth in these examples except insofar as such limitations are specified in the appended claims.

EXAMPLE 1

This example illustrates the process of my invention.

In the example, the triethylamine is used as an acceptor.

A 1-liter flask was equipped with a stirrer, an addition funnel, a thermometer, and a reflux condenser with take-off. A solution of 46.0 g (0.25 m) of $PSCl_3$ in 100 ml of benzene was charged to the flask, followed by the addition of 75 g (0.75 m) of $Et_3N$ in 100 ml of benzene during 1 hour. A solution of 36.0 g (0.50 m) of $Et_2NH$ in 100 ml of benzene was then added during 50 minutes followed by the 40-minute addition of 15.0 g (0.25 m) of $NH_2CH_2CH_2NH_2$ (EDA) in 50 ml of benzene. These latter additions were accompanied by considerable heating and formation of a heavy white precipitate. After standing overnight, the benzene was partially distilled from the mixture prior to filtration. The filtrate was washed with equal volumes of water, 2 N NaOH, and water. The material was returned to the flask and dried by azeotropic distillation of remaining benzene.

The flask was next charged with 250 g (0.20 eq) of polyisobutenylsuccinic anhydride (1060 mol wt, 86.4 sap. no.) and 200 ml of xylene. A slight exothermic reaction was noted. The mixture was refluxed with slow distillation of solvent (90° to 140°C) for 8 hours. It was then filtered and stripped to give 287.2 g of dark brown fluid product. Analysis. Calculated for $C_{99}H_{201}N_4O_2PS$: P, 2.01; S, 2.08. Found: P, 1.22; S, 1.41; Cl, 0.63.

The products produced by the process of the subject invention are substantially the same as the products of copending application Ser. No. 484,024 referred to hereinbefore. Bench tests which show the utility of the products are included in application Ser. No. 484,024. Insofar as necessary in order to demonstrate utility, the disclosure of Ser. No. 484,024 is made a part of this disclosure.

Thus, having described the invention in detail, it will be understood by those skilled in the art that certain variations and modifications can be made without departing from the spirit and scope of the invention as defined herein and in the appended claims.

I claim:

1. A process for preparing compounds represented by the formula

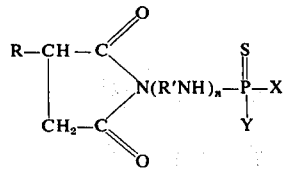

wherein R is alkenyl containing about 10 to about 100 carbon atoms; R' is alkylene containing 1 to about 5 carbon atoms; n is an integer of 1 to 4; X is selected from the group consisting of $NH_2$, NR''R'', and NHR'', and Y is selected from the group consisting of $NH_2$, NR''R''', NHR'', and chloride or bromide ion, wherein in X and Y, R'' is alkyl containing 1 to 16 carbon atos or alkylene polyamino containing 1 to 20 carbon atoms, said process comprising:

a. reacting thiophosphoryl chloride with a monoamine which yields the radical $NH_2$, NR''R'', or NHR'' wherein R'' is alkyl containing 1 to 16 carbon atoms to give a reaction product comprising about 60 to about 100 mole percent phosphorochloridodiamidothioate and about 0 to about 40 mole percent phosphoroamidodichloridothioate, b. reacting the reaction product of step (a) with an alkylene polyamine to give a phosphorotriamidothioate, said alkylene polyamine being represented by the formula

wherein R' is alkenyl containing 1 to 5 carbon atoms and n is an integer of 1 to 4;

c. reacting the phosphorotriamidothioate of step (b) with an alkenyl succinic anhydride or an alkenyl succinic acid, wherein the alkenyl contains about 10 to about 100 carbon atoms; and
d. treating the reaction product of step (c) with a basic material, selected from the group consisting of metal oxide, amine and metal alkoxide, to give the desired product, said process being characterized further in that:
A. step (a) is conducted under the following conditions:
   i. the amount of thiophosphoryl cloride to monoamine, on a molar basis, is in the range of about 1.0 to about 5.0, and
   ii. the temperature is in the range of about 0° to about 110°C.;
B. in step (b) the amount of reaction product of step (a) to amount of polyalkylene amine, on a molar basis, is in the range of 1:0.5 to 1:10; and
C. in step (c) the amount of phosphorotriamidothioate to alkenyl succinic anhydride, on a molar basis, is about 1:0.5 to about 1:2.5.

2. The process of claim 1 wherein R'' of the monoamine used in step (a) is alkyl containing 2 to 6 carbon atoms.

3. The process of claim 2 wherein an alkenyl succinic anhydride is used in step (c).

4. The process of claim 3 wherein the alkylene polyamine of step (b) is ethylene diamine.

5. The process of claim 1 wherein in step (b) an inert solvent is employed.

6. The process of claim 5 wherein step (c) is conducted under the following conditions:
   i. an aromatic solvent, which forms an azeotrope with water, is used, and
   ii. the temperature is near the boiling point of the solvent.

7. The process of claim 6 wherein R'' of the monoamine used in step (a) is alkyl containing 2 to 6 carbon atoms.

8. The process of claim 7 wherein an alkenyl succinic anhydride is used in step (c).

9. The process of claim 8 wherein the alkylene polyamine in step (b) is ethylene diamine.

* * * * *